United States Patent
Perdijon

[11] 4,151,752
[45] May 1, 1979

[54] DEVICE FOR THE EXCITATION OF WAVES AND ESPECIALLY ULTRASONIC WAVES INCLUDING A CELL

[75] Inventor: Jean Perdijon, Saint-Ismier, France

[73] Assignee: Commissariat a l'Energie Atomique, Paris, France

[21] Appl. No.: 754,697

[22] Filed: Dec. 27, 1976

[30] Foreign Application Priority Data

Jan. 6, 1976 [FR] France ............... 76 00185

[51] Int. Cl.² ............. G01N 29/04; G01N 21/32; G02B 3/04
[52] U.S. Cl. ................... 73/642; 350/189; 350/193
[58] Field of Search ............ 356/72, 237, 239; 350/96 C, 160 R, 175 LD, 175 FS; 343/753, 909; 73/67.8 R, 67.8 S, 71.5 R, 71.5 US, 642–644; 310/335; 340/8 L

[56] References Cited
U.S. PATENT DOCUMENTS

| | | | |
|---|---|---|---|
| 3,166,731 | 1/1965 | Joy | 73/67.8 S |
| 3,916,675 | 11/1975 | Perdijon | 73/67.8 S |
| 3,924,453 | 12/1975 | Clark et al. | 73/67.8 S |

FOREIGN PATENT DOCUMENTS

708234  4/1954  United Kingdom ............... 73/67.8 S

Primary Examiner—John K. Corbin
Assistant Examiner—Wm. H. Punter
Attorney, Agent, or Firm—Lane, Aitken & Ziems

[57] ABSTRACT

The device comprises a lens and a source for emitting a beam of parallel light rays or ultrasonic rays at right angles to a flat dioptric element. The lens surface which is located opposite to the radiation-emitting source is flat and the lens surface located opposite to the dioptric element is such that the refracted rays are incident upon the dioptric element at a constant angle. The wave which is incident upon the dioptric element and corresponds to the beam refracted from the lens and the wave refracted from the dioptric element and corresponding to the incident wave are in phase along a predetermined path on the surface of the dioptric element.

4 Claims, 6 Drawing Figures

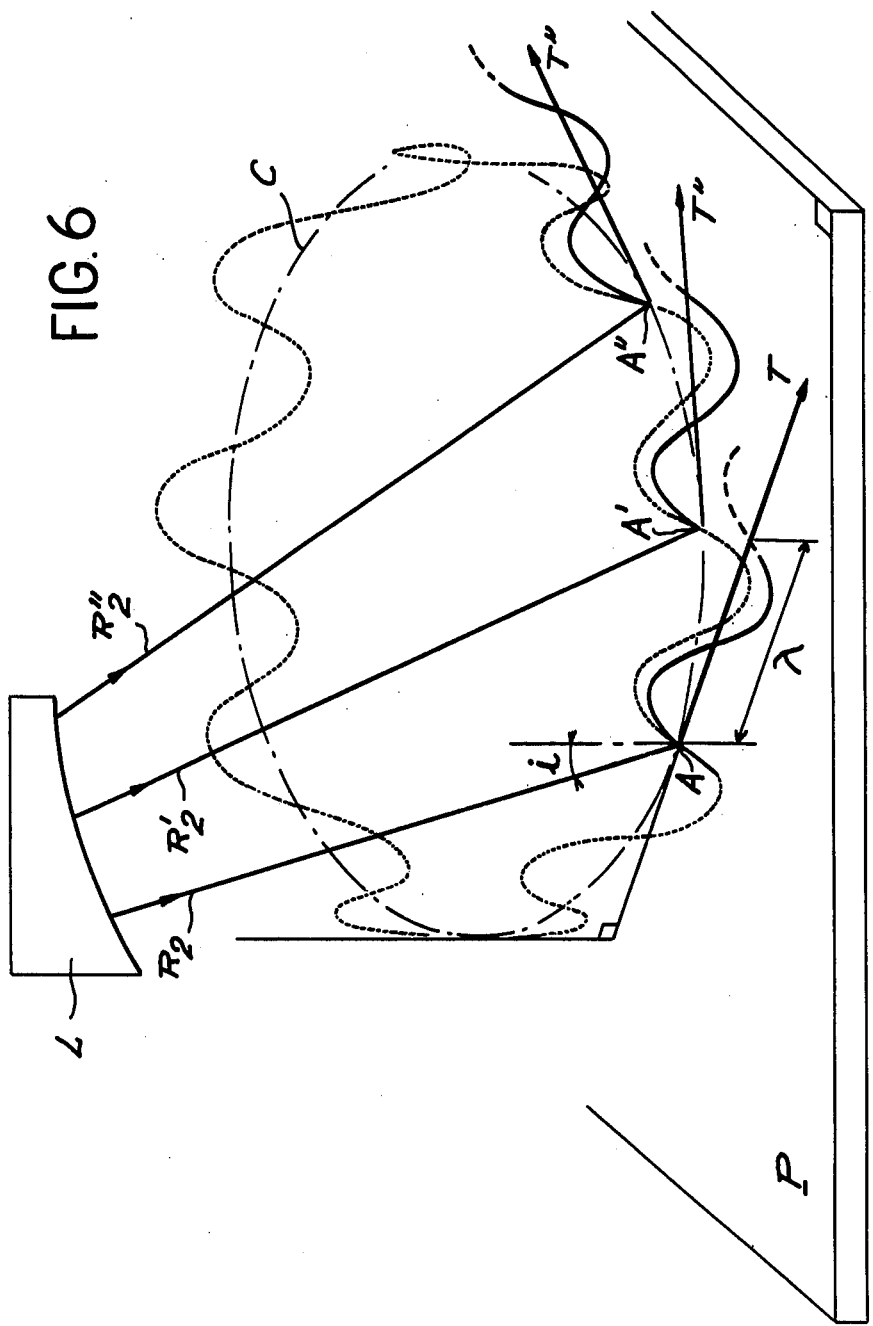

DEVICE FOR THE EXCITATION OF WAVES AND ESPECIALLY ULTRASONIC WAVES INCLUDING A CELL

This invention relates to a wave-excitation device comprising a lens wherein rays and especially light or ultrasonic rays emitted by a source in the form of plane waves are refracted from said lens so as to produce a beam of waves which propagates in a couplant medium placed between the lens and a flat dioptric element. The surface of said lens is such that the wave which is incident upon said flat dioptric element and the wave refracted from the dioptric element are in phase along the paths which are constituted in particular by concurrent straight-line segments or circles, said paths being contained within the plane P of the flat dioptric element.

As is already known, it often proves necessary to excite waves in phase in given directions within a medium limited by a flat face, especially in order to observe any possible flaws in the flat face or plate when ultrasonic waves are employed. The flaws in metallic plate are more clearly observed when the waves which are intended to be reflected from such flaws propagate at right angles to these latter within the plate. In point of fact, the direction of these flaws is not usually known beforehand. It is therefore necessary to send into the medium constituting the plate waves which propagate at a number of different angles in order to ensure efficient detection of these flaws.

This is the case in particular when it is desired to observe flaws by producing Lamb waves in flat plates for testing the soundness of the plates or more particularly of welded zones.

Since it is thus necessary in accordance with known practice at the time of ultrasonic inspection and testing of plates to sweep the surface with ultrasonic waves which propagate in at least two or even four directions in order to detect any possible flaws in almost any orientation, the devices of the prior art usually comprise carriages adapted to carry four transducers having perpendicular planes of incidence. This type of device entails the need for rather cumbersome electronic circuitry for detecting signals which are received after reflection from the flaws.

The aim of the present invention is to solve the problem which consists in finding a method of associating a lens with a single transducer so as to ensure that the waves excited in a medium have varied directions or, better still, so as to ensure that the directions of propagation of the waves within said medium sweep an angle of $2\pi$ radians when it proves possible to do so. As a result, in the case of application to the detection of flaws, at least one wave impinges upon the flaw at right angles to this latter.

This invention makes it possible to provide a device which solves the problem under consideration, which is easy to construct and is limited in capital outlay.

The device for excitation of waves in accordance with the invention comprises a source for emitting a beam F of rays which are parallel to each other (light rays or ultrasonic rays) and a lens. The rays of the beam F are perpendicular to a flat dioptric element P. Said flat dioptric element limits the top surface of the body in which it is desired to induce or excite waves. That surface of the lens of the device in accordance with the invention which is located opposite to the transducer is flat. The second lens surface located opposite to the flat dioptric element is such that the rays of the beam refracted from said second surface after passing through the lens having an index of refraction n arrive at the flat dioptric element P at a constant angle of incidence i; furthermore, the second lens surface is such that the wave which is incident on said dioptric element and corresponds to said ray of the beam refracted from the lens, and the wave refracted from said dioptric element corresponding to said incident wave are in phase along given paths. By way of example, said paths are constituted by concurrent straight-line segments or concentric circles.

In one embodiment of the invention, it is desired to excite waves in phase along straight-line segments which are concurrent in a point. With this objective, it is possible to employ a flat transducer and, in accordance with the invention, a lens whose second surface is a conical surface having a semivertical angle of $\pi/2 - \alpha$ or $\pi/2 + \alpha$, depending on whether it is desired to excite divergent waves or convergent waves, $\alpha$ being such that tangent $$\alpha = \frac{\sin i}{|\cos i - n|}$$

or in fact tan $$\alpha = \frac{\sin i}{\cos i - n}$$

if the relative index of refraction of the medium constituting the lens with respect to a medium placed between the flat dioptric element and the second surface of said lens is smaller than 1 and tan $$\tan \alpha = \frac{\sin i}{n - \cos i}$$

if n is greater than 1.

In another embodiment of the invention, the lens which is intended to ensure phase equalization of the incident and refracted waves permits said phase equalization along a closed curve marked on the surface of the flat dioptric element P. Said surface can be defined by its normal $\vec{m}$ at any point of said surface which:

is contained in a plane $\pi$ at right angles to the flat dioptric element P and tangent to said closed curve, makes an angle $\alpha$ with the axis Oz at right angles to the plane P, the angle $\alpha$ being defined by the relation $$tg\, \alpha = \frac{\sin i}{|\cos i - n|}.$$

In order to excite waves of substantial amplitude within the medium limited by the flat dioptric element P in the case of closed curves, it is an advantage to adjust the frequency of vibrations of said ultrasonic wave in order to ensure that the wavelength associated with the refracted waves in the medium concerned and divided by the sine of the angle of refraction r is a submultiple of the length of said closed curve. The perimeter of the closed curve must in fact be a multiple of the distance between two consecutive equal-phase surfaces which are measured, not along a refracted radius but along the closed curve. In the case of Lamb waves, $r=90°$, sin $r=1$ and the perimeter of the closed curve is a multiple of the wavelength $\lambda$. Thus, at the end of travel along said curve, the waves are added in phase by cyclic resonance effect.

Further properties and advantages of the invention will become more readily apparent from the following description of exemplified embodiments which are given by way of explanation and not in any limiting sense, reference being made to the accompanying drawings, wherein:

FIG. 6 is an explanatory diagram showing the condition of resonance for attaining substantial amplitudes in the case of waves induced within the material which is limited by the flat dioptric element P.

Figure 1:
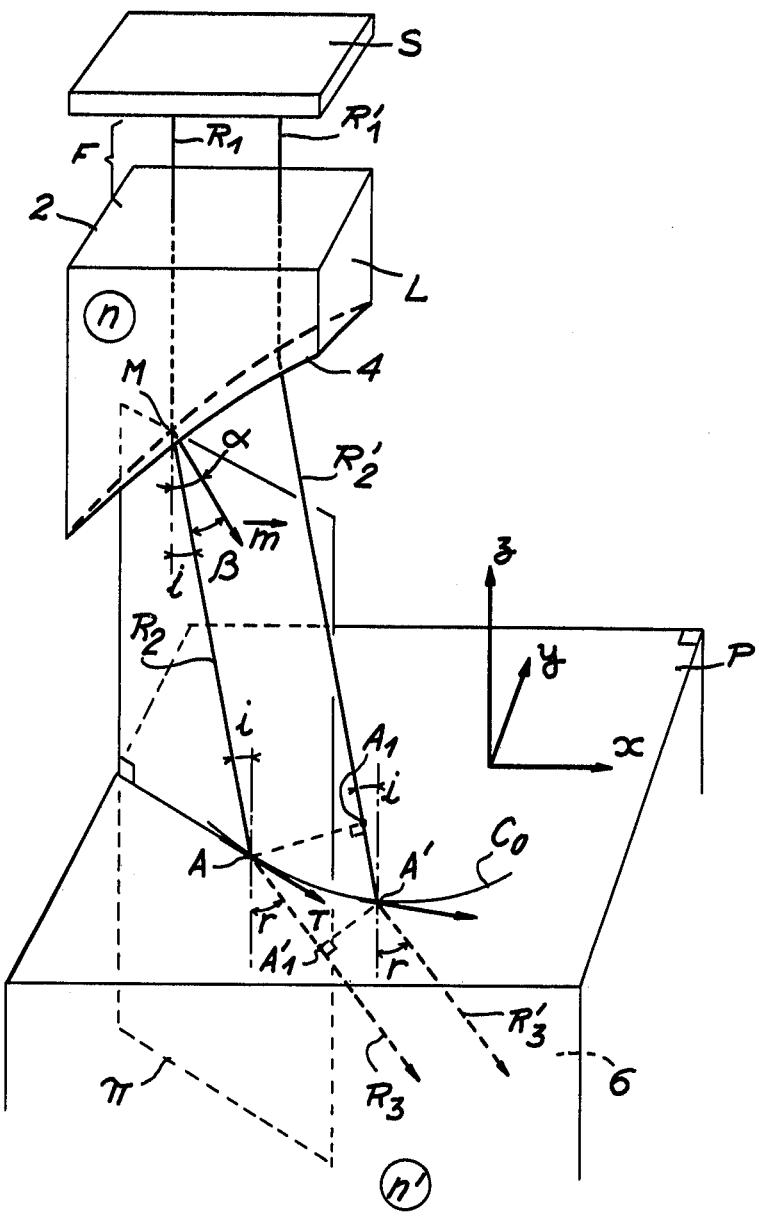
FIG. 1 is an explanatory diagram showing the geometrical structure of the lens and the characteristics of the device in accordance with the invention.

There is shown in FIG. 1 a device in accordance with the invention for phase equalization of the incident waves refracted from the flat dioptric element P along any given curve $C_0$ which may be polygonal. The device comprises a source S for emitting a beam F of parallel rays such as those designated by the references $R_1$ and $R'_1$. The lens L has a first flat face 2 located opposite to the wave source S and a second surface 4 for converting the beam F comprising the rays $R_1$ and $R'_1$ among others into a beam of rays refracted from said second surface 4 and comprising the rays such as those designated by the references $R_2$ and $R'_2$. These rays impinge upon the medium 6 which is limited by the flat dioptric element P at A and A', thus exciting waves within said medium 6. The rays refracted from the flat dioptric element P and corresponding to excitation of the waves within said medium 6 are represented schematically by the rays $R_3$ and $R'_3$. The surface 4 of the lens L is such that the angle of incidence i of the rays $R_2$ and $R'_2$ on the flat dioptric element P is constant. Furthermore, the incident waves refracted from the dioptric element P are in phase. The second surface 4 of the lens L is defined by the orientation of the normal $\vec{m}$ at the point M (the point M corresponds to the incidence of the ray $R_2$ at the point A of the curve $C_0$ which is marked on the flat dioptric element P) and by a second condition of equality of length of the optical paths as will be defined hereinafter.

The plane $\pi$ which passes through A and contains the tangent T to the curve $C_0$ contained within the flat dioptric element P is associated with each point A of said curve $C_0$. Said plane $\pi$ contains the ray $R_2$, the normal at A to the plane P which is parallel to Oz as well as the ray $R_1$ which passes through the point M. In accordance with the first law of Descartes, the normal $\vec{m}$ to the surface 4 of the lens L is also contained within said plane $\pi$ since the incident ray $R_1$ and refracted ray $R_2$ are contained within said plane. The normal m to the point M of the surface 4 makes an angle $\alpha$ with the vertical direction, namely the axis Oz. The refractive index n is the relative index between the medium which constitutes the lens L and the couplant medium which is located between the flat dioptric element P and the surface 4; the second law of Descartes makes it possible to write if $n<1$:

$$n \sin \alpha = \sin \beta = \sin (\alpha - i),$$

where $\beta$ is the angle of refraction in the couplant medium and, if $n>1$:

$$n \sin \alpha = \sin \beta = \sin (\alpha + i).$$

The solution of this equation in $\alpha$ is such that the angle which defines the normal $\vec{m}$ obtained by solution of the previous equation is:

$$tg\, \alpha = \frac{\sin i}{|\cos i - n|}$$

The mode of operation which permits of geometrical construction of the lens 4 is as follows. The value of the angle i is fixed (for example in order to excite Lamb waves in the flat dioptric element P), thus determining the angle $\alpha$ by means of the relation given above and determining point by point the direction of the normal $\vec{m}$ to the surface 4.

It can readily be demonstrated that the refracted wave and the incident wave along the curve $C_0$ are in phase. In fact, in the case of any given curve $C_0$, the segment AA' will be adopted as elementary path, namely that portion of curve which coincides with the direction of the tangent T to the curve $C_0$ at the point A. The difference between the optical paths in the case of the rays $R_2$ and $R'_2$ in the couplant medium is equal to $A'A_1$ and, in the case of the radii $R_3$ and $R'_3$ in the medium limited by the flat dioptric element P, is equal to $AA'_1$. If r is the angle of refraction in the medium limited by the flat dioptric element P, the second law of Descartes $\sin i = n' \sin r$ is such that the optical paths $n'AA'_1 = n'AA' \sin r$ and $A'A_1 = AA' \sin i$ are equal and that the waves are thus in phase over the entire path AA' along $C_0$, n' is the relative index of the medium limited by the flat dioptric element P and of the couplant medium.

Figure 2:
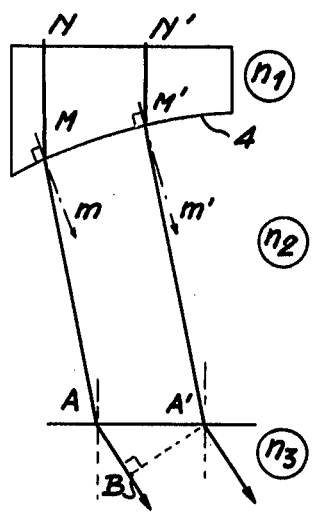
FIG. 2 is an explanatory diagram showing the configuration of the lens L.

There is shown in FIG. 2 a sectional view of the lens L, taken along a plane which is normal to the flat dioptric element P and passes through the segment AA'. The normals at M and M' are as defined earlier and the position of the point M' is such that $n_1(MN) + n_2(MA) + n_3(AB) = n_1(M'N') + n_2(M'A')$. From a knowledge of the curve C and the refractive indices $n_1$, $n_2$ and $n_3$, it is possible to construct the surface 4 of the lens L point by point by means of the equality which has just been mentioned and defines the positions of the points of the surface of the lens L and the orientation of the normals to the surface of said lens.

Figure 3:
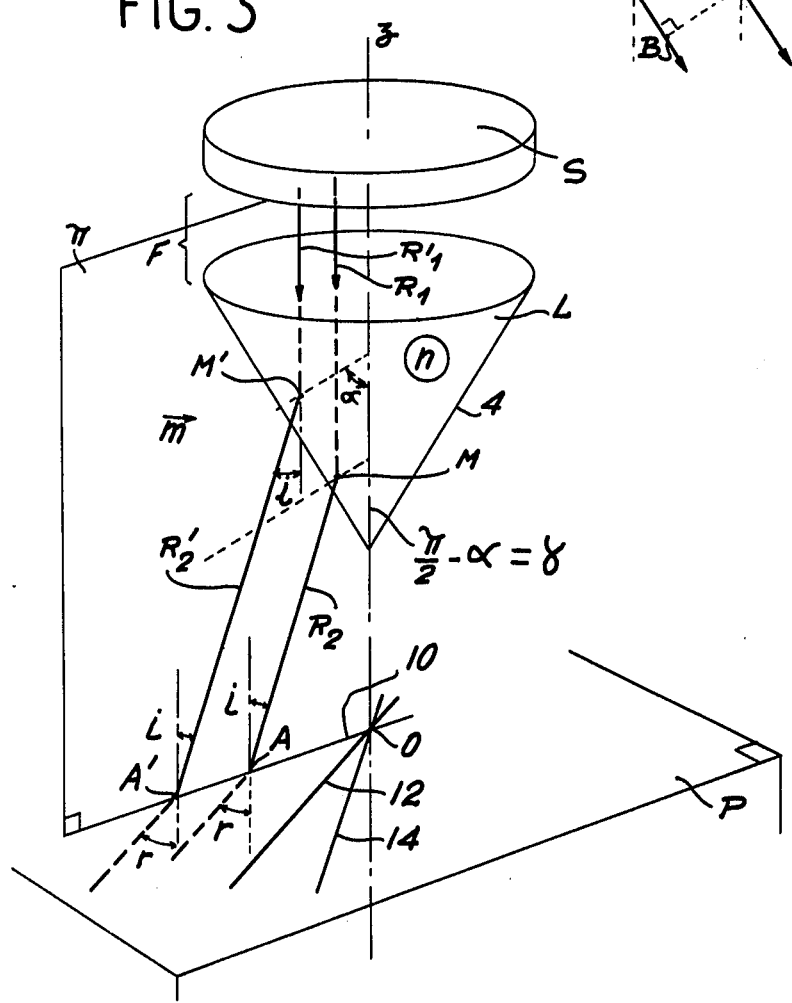
FIG. 3 is a diagram of a lens for exciting waves in concurrent straight-line segments.

In FIG. 3, there is shown a particular embodiment of the invention for exciting in the medium limited by the flat dioptric element P waves which are equalized in phase along segments which are concurrent in a point O such as the segments along the straight lines 10, 12, 14. The device has symmetry of revolution with respect to the axis Oz, thus making it possible to study only what takes place in a plane $\pi$ which passes through said axis. The radiation source S emits a beam F of rays $R_1$ and $R'_1$ refracted from the second surface 4 of the lens L which has the shape of a cone frustum and a semivertical angle $\gamma$ $\pi/2 - \alpha$. The rays $R_2$ and $R'_2$ which are refracted from said second surface 4 impinge upon the surface constituted by the flat dioptric element P at a constant angle of incidence i, thus resulting in an angle of refraction r which is also constant. Compared with FIG. 1, the curve $C_0$ in this embodiment is a straight line which passes through O. It can readily be established that the incident and refracted waves are in phase along straight lines such as the lines 10, 12, 14 which are marked on the plane P. In this embodiment, the normal $\vec{m}$ to the second surface 4 of the lens L also makes an angle $\alpha$ with the axis Oz, said angle $\alpha$ being also defined by the relation $$tg\ \alpha = \frac{\sin i}{|\cos i\ 1\ n|}.$$

Since the entire device has symmetry of revolution about the axis Oz as already mentioned, it is apparent that the waves excited in the medium which is limited by the dioptric element P are in phase along an infinity of straight lines (consisting in practice of straight-line segments) which are concurrent in a point O.

In this embodiment, the waves excited in the medium which is limited by the flat dioptric element P are waves which diverge from the point O.

Figure 4:
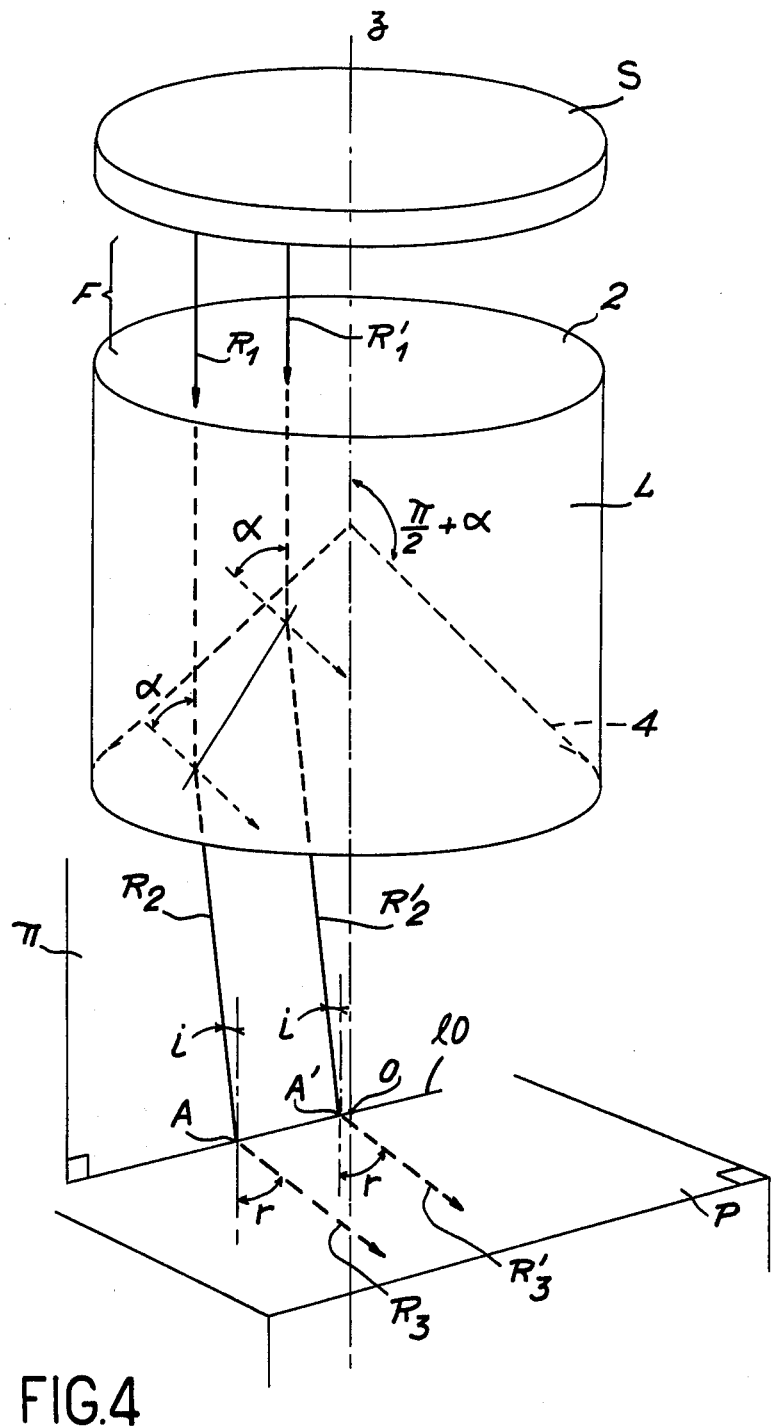
FIG. 4 shows a planoconical lens for exciting convergent waves in the medium limited by the flat dioptric element P.

In FIG. 4, there is shown another embodiment of the device in accordance with the invention for exciting waves which propagate within the medium limited by the dioptric element P in convergent waves. The references which are adopted in FIG. 4 and are the same as those adopted in FIGS. 1 and 2 designate identical elements. In this case, the lens L is constituted by a flat surface 2 and a conical surface 4. The conical surface has a semivertical angle $\pi/2+\alpha$. The rays $R_2$ and $R'_2$ contained within the plane $\pi$ which passes through the axis Oz meet the straight line 10 at a constant angle of incidence i and are in phase with refracted waves corresponding to the rays $R_3$ and $R'_3$ along said straight line 10. The line 10 is defined by the intersection between the plane $\pi$ and the flat upper surface of the element P.

Figure 5:
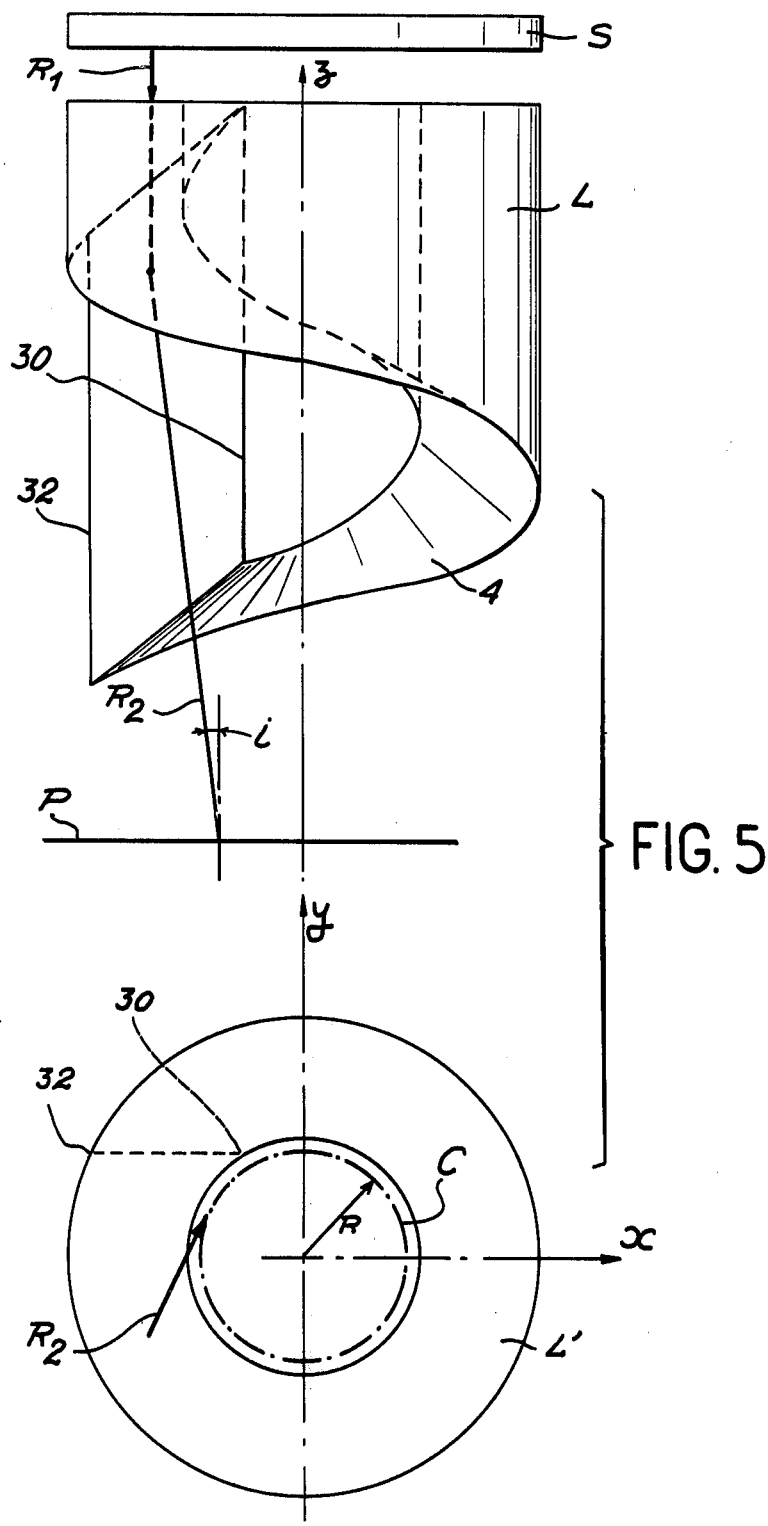
FIG. 5 shows a lens in which the second surface is a "screw" surface for exciting waves which are equalized in phase along a circle C on the flat dioptric element P.

In FIG. 5, there is shown an embodiment of the device according to the invention for exciting waves in phase at the constant angle of incidence on a closed curve such as a circle C having a radius R which is marked on a flat dioptric element P. The surface 4 of the lens L is represented by the following equation in semi-polar coordinates:

$$\rho^2 = (z\ cot\ g\ \alpha + R\ \theta)^2 + R^2$$

wherein the axes Oxyz are as shown in FIG. 4. The structure L' corresponds to a bottom view of the lens L of FIG. 5.

The rays such as $R_1$ emitted by the source S gives rise to rays such as $R_2$ which impinge upon the flat dioptric element P at points of incidence which are distributed along the circle C. These rays such as the ray $R_2$ arrive at the same angle of incidence i and the waves which are incident on and refracted from the flat dioptric element P are in phase along the circle C, which is the particular case of the curve $C_0$ of FIG. 1. In this example of construction, the lens L is limited by two coaxial cylinders 30 and 32 having an axis Oz. In addition and as a result of the shadow, the surface 4 is limited to a single pitch ($\theta_0 < \theta < \theta_0 + 2\pi$).

In FIG. 6, there is shown the structure of incident waves refracted from the flat dioptric element P in the case in which the medium limited by said flat dioptric element P is a flat plate, the angle of incidence i being chosen in known manner so as to excite Lamb waves within the material which constitutes said plate. The structure shown in FIG. 6 corresponds to a lens L as illustrated in FIG. 1. The Lamb waves which are excited at the point A propagate along the tangent T to the circle C. Similarly, the waves excited at A' travel along the tangent T' and the waves excited at A" travel along the tangent T".

The Lamb waves derived from each of the points AA'A" are rapidly destroyed by interference as soon as the distance from the circle C increases in the outward direction. On the other hand, the amplitude of said waves is added along the circle C since there is a maintenance of phase between incident wave and refracted wave along this path, namely a circle in this instance. As is the case with all vibrational phenomena, it is only necessary to ensure that this phase equalization is achieved to within an approximation of one-quarter of a wavelength in order to ensure efficacious phase equalization along the path, in which case phase equalization is achieved along a ring located outside the circle C and corresponds to this phase-displacement.

As has been mentioned in the foregoing, if the wavelength $\lambda$ (in the case of Lamb waves it is not necessary to divide $\lambda$ by sin r since r=90°) of the excited waves within the medium limited by the flat dioptric element P is a submultiple of the perimeter $2\pi R$ of the circle C, the waves which propagate along said perimeter arrive at A with the same phase as the waves which are excited by a new vibration and propagate along the ray $R_2$ and with addition of amplitudes, thus permitting of resonant excitation along said circle or along closed curves. This results in intense effects which are favorable to the reception of echos produced by flaws having small dimensions.

The description of FIG. 6 applies to Lamb waves but can be extended more generally to any other type of waves in which the angle r is other than 90°.

The device as herein described can also be employed as a resonator for waves induced in the flat dioptric element.

The device in accordance with the invention is particularly applicable to the detection of flaws in plates by exciting Lamb waves in said plates which are limited by a flat dioptric element P. In this case, the radiation source is an ultrasonic transducer which operates as an emitter-receiver in order to collect the echos which are reflected from the flaws and circulate along paths which are opposite to the excitation paths. It is readily apparent that, in order to inspect the state of a plate, the transducer-lens unit is displaced along two coordinate axes xy which are parallel to the flat dioptric element P. The device is also applicable to the excitation of mechanical waves other than Lamb waves.

Approximate calculations enable anyone versed in the art to apply this technique to other surfaces for limiting a medium in which it is desired to induce waves in phase, such as cylinders, spheres, tori and the like. The use of the device according to the invention which mainly comprises the lens L can be extended to electromagnetic waves and particle waves. It would be particularly useful in the event that the radiation source S is a laser beam, in which case the structure of the lens L can be employed for the purpose of producing a pencil of refracted light rays corresponding to the characteristics set forth in the foregoing.

It would also be possible within the scope of the present invention to cut the surface of an emitter so as to form a surface at right angles to the rays $R_2$ in order to obtain the same result. In this case, the normal to the surface $\vec{m}$ makes an angle i with Oz (it is only necessary to adopt $n=1$ and $\alpha=i$ in the equations given earlier). However, this design appears to be more costly since the construction gives rise to greater practical difficulty.

One example in which the invention can be carried into effect consists in inspecting a stainless steel plate P having a thickness of 1 mm by means of an ultrasonic transducer in which a frequency of 4 Mc/s is adopted. The excitation of Lamb waves in the $A_1$ mode results in an angle of incidence $i=16.9°$. In the case of an Araldite lens and coupling in water ($n=0.57$), the application of the relation $$tg\,\alpha = \frac{\sin i}{|\cos i - n|}$$

gives a value of the angle $\alpha=36.9°$.

These Lamb waves propagate in steel at a velocity of 5150 m/s, namely a wavelength $\lambda=1.288$ mm. If $2\pi R=10\lambda$ is adopted in order to have resonant excitation, $R=2.05$ mm is obtained (the use of an emitter having a variable frequency makes it possible to adjust the frequency in order to obtain the desired resonance).

In FIG. 4, there is shown the lens L corresponding to these values of $\alpha$ and of R.

Another definition of this surface which limits the bottom face of the lens L consists in stating that it is a surface generated by a segment in which the line of extension remains tangent to a circular helix having a radius R in which a pitch $p=2\pi R\,tg\alpha=9.67$ mm is described.

What we claim is:

1. A device for excitation of waves in a medium limited by a flat dioptric element P, comprising a radiation source for emitting a beam F of rays which are parallel to each other and perpendicular to the flat dioptric element P, wherein said device comprises a lens in which a first flat surface is located opposite to the radiation-emitting source, the second surface of the lens located opposite to the flat dioptric element being such that the rays of the beam F which are refracted from said second surface arrive on the flat dioptric element P at a constant angle of incidence i and wherein the wave which is incident on said dioptric element and corresponds to said beam which is refracted from the second surface of the lens and the wave refracted from said dioptric element and corresponding to said incident wave are in phase along a given path marked on the surface of the flat dioptric element P, said device being adapted to cause phase equalization of incident and refracted waves along straight-line segments on the flat dioptric element P, said second surface of said lens being a conical surface having an axis at right angles to the flat dioptric element P and having a semivertical angle $\pi/2-\alpha$, where $\alpha$ is such that $$tg\,\alpha = \frac{\sin i}{|\cos i - n|},$$

where n is the relative index of refraction of the medium constituting the lens with respect to the medium located between the second surface of the lens and the flat dioptric element P.

2. A device for excitation of waves in a medium limited by a flat dioptric element P, comprising a radiation source for emitting a beam F of rays which are parallel to each other and perpendicular to the flat dioptric element P, wherein said device comprises a lens in which a first flat surface is located opposite to the radiation-emitting source, the second surface of the lens located opposite to the flat dioptric element being such that the rays of the beam F which are refracted from said second surface arrive on the flat dioptric element P at a constant angle of incidence i and wherein the wave which is incident on said dioptric element and corresponds to said beam which is refracted from the second surface of the lens and the wave refracted from said dioptric element and corresponding to said incident wave are in phase along a given path marked on the surface of the flat dioptric P, said device being adapted to cause phase equalization of incident and refracted waves along straight-line segments on the flat dioptric element P said second surface of said lens being a conical surface having a semivertical angle $\pi/2+\alpha$, where $\alpha$ is such that $$tg\,\alpha = \frac{\sin i}{|\cos i - n|},$$

where n is the relative index of refraction of the medium constituting the lens with respect to the medium located between the second surface of the lens and the flat dioptric element P.

3. A device for excitation of waves in a medium limited by a flat dioptric element P, comprising a radiation source for emitting a beam F of rays which are parallel to each other and perpendicular to the flat dioptric element P, wherein said device comprises a lens in which a first flat surface is located opposite to the radiation-emitting source, the second surface of the lens located opposite to the flat dioptric element being such that the rays of the beam F which are refracted from said second surface arrive on the flat dioptric element P at a constant angle of incidence i and wherein the wave which is incident on said dioptric element and corresponds to said beam which is refracted from the second surface of the lens and the wave refracted from said dioptric element and corresponding to said incident wave are in phase along a given path marked on the surface of the flat dioptric element P, said device being adapted to cause phase equalization of incident and refracted waves along a circle C having a radius R marked on the flat dioptric element P, said second surface of said lens being such that the normal $\vec{m}$ at all points of said surface is contained in a plane $\pi$ at right angles to the flat dioptric element P and tangent to said circle C and makes an angle $\alpha$ with an axis Oz at right angles to said flat dioptric element P, the angle $\alpha$ being defined by:

$$tg\,\alpha = \frac{\sin i}{|\cos i - n|},$$

where n is the relative refractive index between the medium constituting said lens and the medium located between the second surface of said lens and the flat dioptric element P, said second surface being described by an equation in semipolar coordinates $\rho^2=(z\,cotg\alpha+R\theta)^2+R^2$, where $\rho$ is the radius and $\theta$ is the radius and $\theta$ is the polar angle.

4. A device for excitation of waves in a medium limited by a flat dioptric element P, comprising a radiation source for emitting a beam F of rays which are parallel to each other and perpendicular to the flat dioptric element P, wherein said device comprises a lens in which a first flat surface is located opposite to the radiation-emitting source, the second surface of lens located opposite to the flat dioptric element being such that the rays of the beam F which are refracted from said second surface arrive on the flat dioptric element P at a constant angle of incidence i and wherein the wave which is incident on said dioptric element and corresponds to said beam which is refracted from the second surface of the lens and the wave refracted from said dioptric element and corresponding to said incident wave are in phase along a given path marked on the surface of the flat dioptric element P, said device being adapted to cause phase equalization of incident and refracted waves along a circle C having a radius R marked on the flat dioptric element P, said second surface of said lens being such that the normal $\vec{m}$ at all points of said surface is contained in a plane $\pi$ at right angles to the flat dioptric element P and tangent to said circle C and makes an angle $\alpha$ with an axis Oz at right angles to said flat dioptric element P, the angle $\alpha$ being defined by:

$$tg\, \alpha = \frac{\sin i}{|\cos i - n|},$$

where n is the relative refractive index between the medium constituting the lens and the medium located between the second surface of the lens and the flat dioptric element P, said second surface being described by an equation in semipolar coordinates $\rho^2 = (z\, cotg\alpha + R\theta)^2 + R^2$, where $\rho$ is the radius and $\theta$ is the polar angle, and wherein the frequency of vibration of the waves emitted by said radiation source is such that the wavelength associated with the refracted waves in the medium limited by the flat dioptric element P divided by the sine of the angle r of refraction within said medium is a submultiple of the length of said circle C which is marked on the flat dioptric element P.

* * * * *